United States Patent [19]

Horne et al.

[11] 4,083,877

[45] Apr. 11, 1978

[54] PREPARATION OF A PEROXIDE

[75] Inventors: David Smith Horne, Warrington; Robert Eric Talbot, Burtonwood; Peter John Russell, St. Helens, all of England

[73] Assignee: Interox Chemicals Limited, London, England

[21] Appl. No.: 683,654

[22] Filed: May 6, 1976

[30] Foreign Application Priority Data

May 13, 1975 United Kingdom ............... 20030/75

[51] Int. Cl.$^2$ ........................................... C07C 179/14
[52] U.S. Cl. ................................................. 260/610 D
[58] Field of Search ......... 260/610 D, 610 SC, 610 R

[56] References Cited

U.S. PATENT DOCUMENTS

| | | | |
|---|---|---|---|
| 1,614,037 | 1/1927 | McKee | 260/610 D |
| 3,674,858 | 7/1972 | Le Barge | 260/610 D |

FOREIGN PATENT DOCUMENTS

| | | | |
|---|---|---|---|
| 1,156,573 | 7/1969 | United Kingdom | 260/610 D |

OTHER PUBLICATIONS

Tobolsky "Organic Peroxides," (1954) pp. 39–40.

*Primary Examiner*—James O. Thomas, Jr.
*Assistant Examiner*—Werren B. Lone
*Attorney, Agent, or Firm*—Larson, Taylor and Hinds

[57] ABSTRACT

The present invention provides a process for making diphthaloyl peroxide by reacting phthalic anhydride with aqueous hydrogen peroxide at a pH controlled to between pH 8 and 10, preferably pH 8.8 to 9.2 and a low temperature preferably maintained at 0° to 5° C, and thereafter removing diphthaloyl peroxide from solution, suitably by acidification and filtration. Preferably excess solid phthalic anhydride is employed and is filtered out before the solution is acidified. Desirably the concentration of active oxygen species is maintained at below 0.3 moles/liter.

Diphthaloyl peroxide is particularly suitable for bleaching/washing fabrics, optionally in conjunction with an inorganic persalt e.g. sodium perborate, at a temperature of from 30° to 60° C.

12 Claims, No Drawings

PREPARATION OF A PEROXIDE

The present invention relates to modifications in or improvements to a process for the preparation of diphthaloyl peroxide.

Hitherto, it has been proposed by A. Baeyer and V. Villiger in 1901 that diphthaloyl peroxide could be produced by reaction between phthalic anhydride and hydrogen peroxide under aqueous alkaline conditions, the solution containing an excess of hydrogen peroxide over the stoichiometric amount. We have found that, in carrying out the reaction, the pH of the solution rapidly falls from an initial value of approximately 13 to about 7. Although no yields were quoted by Baeyer and Villiger, on repetition of their work, we have obtained yields of the order of only 8% of the theoretical maximum. Such yields are commercially unacceptable.

In an attempt to improve reaction yields, we have investigated the reaction paths, and have theorised that there are four major reactions and various other side reactions. The four major reactions are as follows:

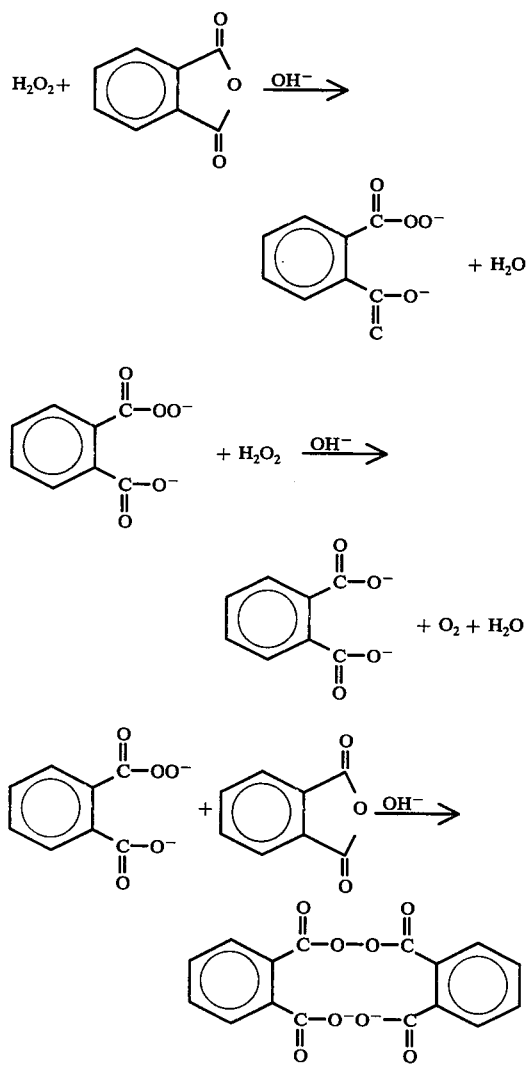

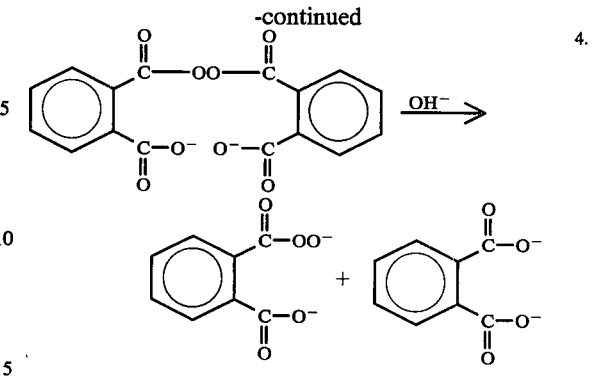

According to this theory, diphthaloyl peroxide is prepared by first forming an intermediate, a monoperoxyphthalate anion, and then reacting the intermediate with a further mole of phthalic anhydride. Reactions 2 and 4 are competitive reactions with reaction 3, and in consequence must be suppressed or retarded in order to obtain diphthaloyl peroxide in a commercially acceptable yield. We have found that the rate of each of the reactions 1 to 4 above is dependent upon the pH and the temperature of the solution, and the concentration of the reactant species therein. In particular, we have found that reaction 3 proceeds more slowly as the pH is lowered and that at pHs of 8 and below it proceeds at an unacceptably slow rate. On the other hand, reaction 4, the hydrolysis of diphthaloyl peroxide under alkaline conditions, proceeds faster as the pH is increased. At pHs of greater than 10, diphthaloyl peroxide hydrolyses so rapidly that it is destroyed substantially as quickly as it can be produced in reaction 3 and consequently only poor yields of diphthaloyl peroxide are obtained.

Furthermore, we have found that in order to favour reaction 3 as opposed to reactions 2 and 4, it is desirable to carry out the reaction at a low temperature.

According to the present invention there is provided a process for the preparation of diphthaloyl peroxide comprising the steps of reacting phthalic anhydride with aqueous hydrogen peroxide under alkaline conditions, controlling both the pH of the solution between 8 and 10, and the temperature of the solution at a low temperature during the period of production of diphthaloyl peroxide, and thereafter recovering diphthaloyl peroxide from the solution. It will be understood that at a pH of from 8 to 10 at least part of the diphthaloyl peroxide is in anion form.

By effecting such a process, it is possible ot obtain improved yields of diphthaloyl peroxide. It is particularly desirable to maintain the pH of the solution at a pH of from 8.8 to 9.2, because at such a pH reaction 3 instead of reaction 4 is most favoured. The pH may be maintained by any conventional method, such as by detecting a fall in pH and in consequence, manually or automatically introducing into the solution a compensatory amount of alkali such as sodium hydroxide. An alternative or additional method is to employ buffers in solution. In practice it is convenient to control the pH of the solution during substantially the whole of the period after the mixing of the reactants during which period reactions 1 to 4 would cause significant change in the pH, if pH control were not effected.

As can be deduced from the reactions hitherto described, the production of diphthaloyl peroxide is believed to proceed via an intermediate. We have found that reaction 1 proceeds smoothly at temperatures in the region of from 0° C to about 40° C and under neutral or mildly alkaline conditions. In general under such conditions reaction 1 proceeds at a rate faster than reactions 2 or 3. In consequence, it is possible to carry out the preparation of diphthaloyl peroxide in two stages, by producing the intermediate in the first step, using the above-mentioned conditions, and thereafter reacting the intermediate with further phthalic anhydride at the low temperature and at the pH controlled between 8 and 10. In practice, it is convenient, however, to carry out the preparation in a single reactor, without separating the two stages, maintaining the temperature throughout at or below about 10° C, and preferably at or below 5° C.

In especially preferred embodiments, a substantial excess of phthalic anhydride over the stoichiometric quantity of 2 moles per mole of hydrogen peroxide is employed. The excess over the stoichiometric quantity is generally at least two moles of phthalic anhydride per mole of hydrogen peroxide and is often in the range of two to three moles. By employing such an excess of phthalic anhydride, instead of the excess of hydrogen peroxide as suggested by Baeyer and Villiger, it is believed that the reaction 2 can be suppressed, thereby enabling a higher proportion of the intermediate to react with further phthalic anhydride to produce diphthaloyl peroxide. In general, it is convenient to introduce solid phthalic anhydride into hydrogen peroxide solution, so that when excess phthalic anhydride is employed it is desirable to interpose a separation stage between the production of the diphthaloyl peroxide, and its recovery. In the separation stage solid phthalic anhydride is removed by suitable techniques such as by filtration or centrifuging and can be recycled. During the separation the temperature of the solution is preferably controlled at or below about 10° C, and desirably at about the temperature at which the preparation was controlled.

The diphthaloyl peroxide can be recovered conveniently by acidfying the solution, suitably by mixture with a dilute mineral acid such as sulphuric acid, until the pH is sufficiently low for the diphthaloyl peroxide to precipitate out. Thorough mixing and cooling can be effected so as to disipate and remove the heat of dilution and neutralisation generated by such acidification. The precipitate can be separated from the solution by conventional techniques such as by filtration, flocculation or centrifuging, and can be washed and dried. Thus, in some particularly preferred embodiments of the present invention, there is provided a process for the preparation of diphthaloyl peroxide comprising the steps of reacting aqueous hydrogen peroxide with phthalic anhydride, present in at least 4 moles per mole of hydrogen peroxide at a temperature controlled at from 0° to 5° C, and at a pH controlled at from 8.8 to 9.2 until at least some diphthaloyl peroxide has been prepared, separating excess phthalic anhydride from the solution, acidifying the solution until diphthaloyl peroxide precipitates from the solution and separating the precipitated diphthaloyl peroxide from the solution. In practice, it is preferable to continue the process for preparation of diphthaloyl peroxide until most of the available oxygen is present in the diphthaloyl peroxide rather than in any other peroxidic species.

Although, in general, any concentration of reactants may be employed and whilst it might be considered to be advantageous to use high concentrations of reactants so that diphthaloyl peroxide is precipitated quickly from solution we have found, surprisingly, that improved yields may be obtained by employing low concentrations of reactants. in particular, we have found it desirable to maintain the active oxygen concentration in solution to below about 5,000 ppm and preferably below 3,000 ppm of active oxygen. Since hydrogen peroxide, the postulated intermediate, and diphthaloyl peroxide each contain only one active oxygen per molecule, it will be understood that this amounts to maintaining the total concentration of such species to below about 0.3 moles per liter, and preferably below about 0.2 moles/liter. In order to make reasonable use of apparatus employed, it is preferable to employ the concentration of from 0.15 to 0.2 moles of active oxygen-containing species per liter.

Furthermore, although substantially all the diphthaloyl peroxide is recovered from solution, we have found that there remains in solution a small proportion of monoperoxyphthalic acid. This can be recovered by washing with an organic solvent such as ether. The active oxygen-containing species can be removed from the organic solvent by washing in aqueous alkali and then returned to the reactor thereby reducing the amount of fresh phthalic anhydride required, and in consequence improving the overall yield of diphthaloyl peroxide, based on the amount of phthalic anhydride consumed.

The preparation of diphthaloyl peroxide as described herein, may be conveniently carried out in a continuous cyclic process or in a batchwise manner. In practice, the size of the equipment, rates of flow of reactants and solution are so arranged that substantially all the hydrogen peroxide is consumed. In general we have found that a reaction period of about half an hour can be sufficient, but that this can vary according to the quantity of the batch.

The diphthaloyl peroxide produced by the preparation described herein may be employed as a polymerisation initiator, particularly in emulsion polymerisation, as a curing agent, in particular for cross-linking water soluble polymers, and as a germicide, in a manner analogous to the use of hydrogen peroxide. It can also be incorporated in bleaching or detergent compositions, in which, either by itself or in conjunction with an inorganic peroxocompound such as sodium perborate tetrahydrate, it acts as a source of monoperoxyphthalic acid, a bleaching agent.

Diphthaloyl peroxide in common with many other organic peroxides, can be sensitive to impact especially when substantially pure and dry, and must be handled with due care and attention. Diluents and coatings with compatible substances may be employed to further reduce any hazard.

A range of which compatible substances is disclosed in our copending application filed herewith. Substantially water insoluble substances such as phthalic acid can be added at any convenient stage, for example to liquor containing precipitated phthaloyl peroxide, whereas water soluble substances such as sodium or magnesium sulphate should preferably be added to washed filter cake.

It is to be understood that the present invention is not dependent upon or restricted to any particular belief, theory or postulate. Such beliefs, theories or postulates included in the present specification are present solely to assist in the understanding of the invention.

Having now described the invention in general terms, one embodiment will now be described more fully by way of example only.

Diphthaloyl peroxide was prepared by adding finely powdered phthalic anhydride (7.2g) gradually over a period of five minutes to a solution of hydrogen peroxide (0.46% by weight, 90 cm$^3$) maintained at a temperature of between 1° to 3° C by the use of a cooling jacket, and the pH of 9 plus or minus 0.2 by dropwise addition of sodium hydroxide sufficient to counteract the generation of acidity as the reaction proceeded. The solution was stirred constantly, so that the proportion of the finely powdered phthalic anhydride which did not go into solution, remained in suspension, and the temperature and pH were controlled for a further 25 minutes, by which time substantially all the hydrogen peroxide had been consumed. The suspension was filtered into sulphuric acid (10% by weight, 30 cm$^3$) and substantially all the diphthaloyl peroxide precipitated out. The solid which had been filtered off was washed with water and then dried to recover phthalic anhydride (3.03g). The acidified filtrate was centrifuged and the precipitate, separated thereby, was washed with water (40 cm$^3$) and dried giving diphthaloyl peroxide (3.1 g). An iodometric assay of the crude product showed that it contained 89.1% of active material, and negligible amount of monoperoxyphthalic acid, giving a reaction yield of 59.4%, based on consumption of phthalic anhydride.

The supernatant liquid from the centrifuge was contacted with ether (3 by 30 cm$^3$) and monoperoxyphthalic acid (0.4 g) was recovered from the ether.

What we claim is:

1. A process for the preparation of diphthaloyl peroxide comprising the steps of reacting phthalic anhydride with aqueous hydrogen peroxide under alkaline conditions, and thereafter recovering diphthaloyl peroxide from the solution controlling both the pH of the solution between 8 and 10, and the temperature of the solution at a temperature of 10° C or below during the period of production of diphthaloyl peroxide.

2. A process according to claim 1 wherein the pH is maintained at from 8.8 to 9.2 during the period of production of diphthaloyl peroxide.

3. A process according to claim 1 wherein the temperature of the solution is maintained at or below 5° C during the period of production of diphthaloyl peroxide.

4. A process according to claim 1 wherein a first stage comprises reaction between hydrogen peroxide and phthalic anhydride to form an intermediate under neutral or mildly alkaline conditions and a second stage comprises production of diphthaloyl peroxide from the intermediate at the controlled pH and low temperature.

5. A process according to claim 1 wherein an excess of at least two moles of phthalic anhydride per mole of hydrogen peroxide over the stoichiometric quantity of two moles per mole of hydrogen peroxide is employed.

6. A process according to claim 1 wherein the concentration of active oxygen-containing species in solution is from 0.15 to 0.2 moles/liter.

7. A process according to claim 1 wherein diphthaloyl peroxide is recovered by acidifying the solution until diphthaloyl peroxide precipitates out.

8. A process according to claim 1 wherein solution from which diphthaloyl peroxide has been recovered is contacted with an organic solvent, and active oxygen-containing species are recovered from the solvent for re-use in the reaction process.

9. A process according to claim 1 wherein phthalic anhydride is present in an amount in excess of stoichiometric.

10. A process according to claim 9 wherein the temperature is maintained at 0° to 10° C.

11. A process according to claim 10 wherein the pH is maintained at 8.8 to 9.2.

12. A process according to claim 11 wherein the temperature is maintained at 0° to 5° C.

* * * * *